(12) United States Patent
Thomas

(10) Patent No.: US 9,569,982 B2
(45) Date of Patent: Feb. 14, 2017

(54) METHODS AND SYSTEMS FOR PROVIDING SELF-CARE AND ACCLIMATION RECOMMENDATIONS TO A CLIENT DEVICE BASED ON ENVIRONMENTAL CONDITIONS

(71) Applicant: Wendy Marie Thomas, Washington, DC (US)

(72) Inventor: Wendy Marie Thomas, Washington, DC (US)

( * ) Notice: Subject to any disclaimer, the term of this patent is extended or adjusted under 35 U.S.C. 154(b) by 191 days.

(21) Appl. No.: 14/333,361

(22) Filed: Jul. 16, 2014

(65) Prior Publication Data

US 2015/0044651 A1    Feb. 12, 2015

Related U.S. Application Data

(60) Provisional application No. 61/846,664, filed on Jul. 16, 2013.

(51) Int. Cl.
*G09B 23/28* (2006.01)
*G09B 19/00* (2006.01)
*G06F 19/00* (2011.01)

(52) U.S. Cl.
CPC ............ *G09B 19/00* (2013.01); *G06F 19/345* (2013.01); *G06F 19/3481* (2013.01)

(58) Field of Classification Search
CPC .................................................... G09B 19/00
USPC ........................................................ 434/247
See application file for complete search history.

(56) References Cited

U.S. PATENT DOCUMENTS

2016/0019813 A1\* 1/2016 Mullen .................. G09B 19/00
434/236

\* cited by examiner

*Primary Examiner* — Kesha Frisby
(74) *Attorney, Agent, or Firm* — K&L Gates LLP

(57) ABSTRACT

Computer implemented methods and systems to provide self-care and acclimation recommendations to a client device based on a unique health profile and environmental conditions.

20 Claims, 2 Drawing Sheets

METHODS AND SYSTEMS FOR PROVIDING SELF-CARE AND ACCLIMATION RECOMMENDATIONS TO A CLIENT DEVICE BASED ON ENVIRONMENTAL CONDITIONS

CROSS-REFERENCE TO RELATED APPLICATIONS

This application claims the benefit from U.S. Provisional Patent Application No. 61/846,664, filed on Jul. 16, 2013, entitiled "METHODS AND SYSTEMS FOR PROVIDING SELF-CARE AND ACCLIMATION RECOMMENDATIONS TO A CLIENT DEVICE BASED ON ENVIRONMENTAL CONDITIONS. The above application is hereby incorporated by reference herein.

BACKGROUND

Field of Invention

The present invention relates generally to providing self-care recommendations to a person experiencing a change in environmental conditions, and more particularly, to provide such recommendations based in part on the person's unique health profile.

Related Art

Environmental conditions have long been known to affect human health. Extreme weather such as hurricanes, tornados, and floods are most commonly associated with threats to human life yet more common and subtle environmental conditions have a significant impact on human health, especially for people suffering from chronic diseases.

Human adaptation to a changing climate system is essential for promoting healthy and productive societies. Since our adaptation capacity is a function of age, health condition, and also the rate of environmental change, there is a need to inform individuals on how to thrive amid current shifts in our planet's fluid systems (e.g., climate, weather, and water). It is known that these systems are in state of unusual imbalance due to both natural and anthropogenic influences. Based on physics, these inputs into the system can generate more frequent and/or intense extreme weather events (e.g., excessive heat or cold temperatures, lower cloud levels that trap pollutants, rise in algal blooms, etc) in order to restore balance within Earth's fluid bodies. With the driving force of planetary dynamics being balance, the more disequilibrium that is present in a system means that there will be more restoring forces (e.g., extreme or anomalous weather) in order to bring about that balance.

The balance restoring force manifests as weather, which today is changing on time and space scales that humans have not yet experienced. During previous climatic shifts, humans were able to migrate away from such changes, lacked a protective built environment (e.g., heated or air conditioned homes) and their environmental changes tended to be more gradual in onset. Today, we live in non-migratory societies where we are subject balancing forces. Healthy individuals can take up to a decade to adapt to seasonal shifts, so when they travel or move to a new location it will take time to acclimate to the new environment. Chronically ill individuals have more challenges to adaptation because the range of environmental supports (e.g., clean air, mild temperatures, etc) are lacking.

SUMMARY

Aspects of the present invention are directed to novel computer implemented methods and systems to provide self-care and acclimation recommendations to a client device based on a unique health profile and environmental conditions.

In some embodiments, a client device is configured to automatically transmit at a predefined time interval or on the demand of a user, a location (e.g., city and state, zip code, latitude/longitude, etc.) and a unique identifier of a person associated with a health profile. This transmission may be through a data network to a remote computer.

In some further embodiments, a remote computer is configured to receive the current (or sometimes expected future) location of a person through a client device and associate that person (through their unique identifier) with a health profile which may be stored in a database.

A rules engine running on the remote computer may then associate current and forecasted environmental conditions received from a data provider for the current (or future) location of a person associated with or linked to the unique identifier and health profile and use that information along with a set of rules and medical best practices to generate self-care or acclimation recommendations. The remote computer may then transmit those recommendations through a data network to a client device to be displayed to a user.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION

Figure 1:
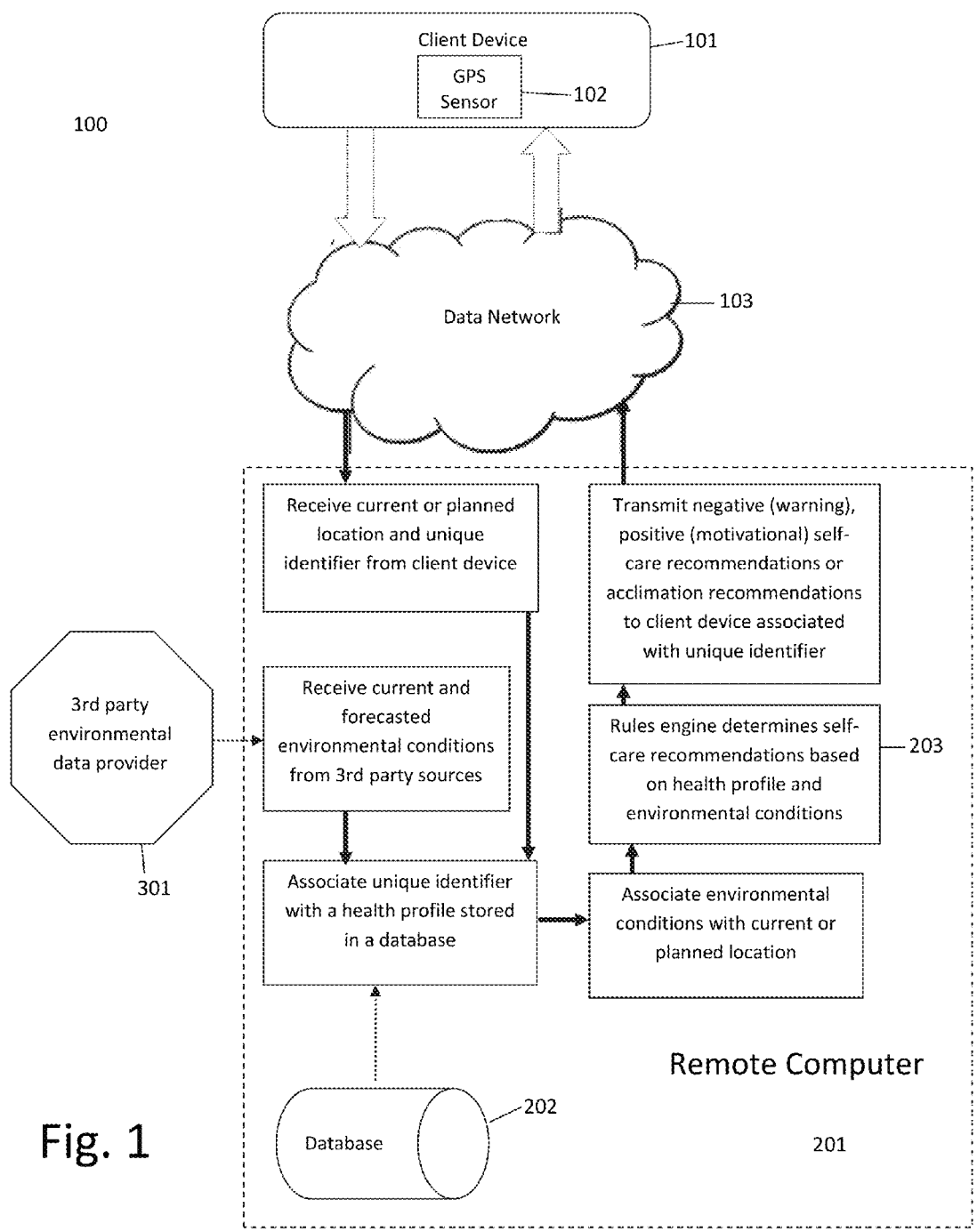
FIG. 1 shows one example of the system and methods of the present invention.

The terminology used herein is for the purpose of describing particular embodiments only and is not intended to be limiting of the claimed invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing aspects and embodiments of the present invention(s), it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New methods and systems to provide self-care and acclimation recommendations to a person through a client device are discussed herein. In the following description, for purposes of explanation, numerous specific details are set forth. It will be evident, however, to one skilled in the art that the disclosed aspects and embodiments may be practiced without these specific details.

As used herein, the term "computer" refers to a machine, apparatus, or device that is capable of accepting and performing logic operations from software code.

A "remote computer" as used herein means a type of computer that is in a different location from a client device. An example of a remote computer may be a server. The term "software", "software code" or "computer software" refers to any set of instructions operable to cause a computer to perform an operation. Software code may be operated on by a "rules engine" or processor. Thus, the methods and systems of the present invention may be performed by a computer based on instructions received by computer software.

The term "client device" as used herein is a type of computer which is operated by a person. Non-limiting examples of client devices may include; personal computers (PCs), workstations, laptops, tablet PCs including the ipad, cell phones including iphones and android phones, or generally any electronic device capable of running computer software and displaying information to a user. In some preferred embodiments, a client device comprises a global positioning system (GPS) or GPS sensor.

As used herein, the term database means a digital collection of information. The present invention uses novel methods and processes to link, modify, and display information stored in a database such as a health profile with a specific user, a location, and environmental conditions. For the purposes of the present disclosure, a database may be stored on a server and accessed by a client device through the internet (i.e., the database is in the cloud) or alternatively in some embodiments the database may be stored on the client device or remote computer itself (i.e., local storage).

As used herein the term "self-care recommendations" shall mean specific actions a person may take to maintain or improve a healthy body. These recommendations may be positive (motivational) in nature or negative (warnings). Some non-limiting examples of positive actions comprise: exercising, eating healthy, networking with family or friends, taking vitamins or supplements, etc. Some non-limiting examples of self-care actions that are warnings or negative in nature may comprise; taking medications, avoiding the sun, staying indoors, wearing sunscreen, packing an inhaler, cleaning an air filter, washing hands, practice calmed breathing, nasal breathing, nasal/mouth breathing, increasing or decreasing fluid consumption, etc. In some embodiments of the present invention, self care recommendations are sent to a user through a data network and displayed onto a client device.

As used herein the term "acclimation recommendations" shall mean specific actions a person may take to help acclimate their body to new and unfamiliar environmental conditions. Some non-limiting examples of acclimation recommendations include; changing fluid consumption levels, eating particular foods, avoiding sun exposure between certain hours, wearing sun screen, avoiding strenuous activity, wearing particular clothing, etc. In some embodiments of the present invention, acclimation recommendations are sent to a user through a data network and displayed onto a client device.

As used herein, the term "environmental conditions" or sometimes "environmental data" shall mean the general condition or data related to the air and/or water (or general environment) at a certain location and may include conditions such as; weather (as defined below), water body conditions, UV index, ozone levels, allergen and mold particle counts, etc., as well as the social environment relating to safety and crime.

As used herein, the term "weather" shall mean a type of environmental condition and may include things like; temperature, precipitation, wind speed, wind direction, humidity, relative humidity, cloud cover, sun exposure etc.

As used herein the term "health profile" shall mean general and medical information about a person, and may comprise things like: age, gender, race, height, weight, body mass index, medical history, family medical history, chronic diseases, home location or residence, etc.

As used herein the term "chronic diseases" shall include but not be limited to the following list of diseases; Acquired Immune Deficiency Syndrome (AIDS), Attention Deficit/Hyperactivity Disorder (ADHD), Allergies, Amyotrophic Lateral Sclerosis (ALS), Alzheimer's Disease, Arthritis, Asthma, Behcet's syndrome, Bipolar Disorder, Bronchitis, Cancer, Cardiomegaly, Cardiomyopathy, Crohn's disease, Chronic cough, Chronic Fatigue Syndrome (CFS), Chronic Obstructive Pulmonary Disease (COPD), Congestive Heart Failure, Cystic Fibrosis, Depression, Diabetes, drug addiction, alcohol addiction, Emphysema, Fibromyalgia, Gastroesophageal reflux disease (GERD), Gout, Hansen's Disease, Hunter syndrome, Huntington's disease, Hypertension, Marfan syndrome, Mesenteric lymphadenitis, Multiple Sclerosis, Migraines, Myelofibrosis, Nephrotic syndrome, Obesity, Parkinson's disease, Pneumoconiosis (interstitial lung diseases), Pulmonary edema, Pulmonary Fibrosis, Pulmonary hypertension, Reactive airway disease, Sarcoidosis, Scleroderma, Systemic Lupus Erythematosus, Ulcerative colitis, etc.

In some aspects of the present invention, computer-implemented methods and systems are disclosed. These provide self-care recommendations and acclimation recommendations (collectively, self-care recommendations) to a person through a client device and are based in-part on the person's location (i.e., their physical location on the planet) and their health profile.

In some embodiments perhaps best shown by FIG. 1, a system 100 comprises one or more client devices 101 with may contain a GPS sensors 102, a data network 103, a remote computer 201, one or more 3rd party environmental data providers 301, a database 202, and a rules engine 203.

Referring to FIG. 1, in some embodiments, a client device 101 comprising a GPS sensor 102 is configured to receive specific location information based on coordinates provided by a satellite. The client device 101 transmits the received location information along with a unique identifier (i.e. IP address, MAC address, login name, unique number, unique letter(s), unique string of integers, unique name, unique email address, etc.) to a remote computer 201 (e.g., a server) through a data network 103 (e.g., the internet, a wifi network, a cellular network, a local area network, etc.).

The remote computer 201 is configured to run operations (i.e., software code) which will associate the received location information and unique identifier to a health profile stored in a database 202. The database 202 may be located on the same remote computer 201 (as shown) or on a separate computer (not shown) and accessible through a data network 103. The remote computer 201 is also configured to receive environmental condition data and environmental forecasts from a 3rd party providers 301 such as commercial providers (e.g., The Weather Chanel™) or non-commercial providers (e.g., The National Oceanic and Atmospheric Administration).

In some embodiments, the remote computer 201 runs operating code configured to associate or link a health profile stored in a database 202 to a unique identifier which is linked or associated to a current or planned location (i.e., a physical location on the planet of a person). A rules engine 203 operating on the remote computer 201 and based on operational code instructions is configured to generate self-care recommendations specific for each health profile and one or more environmental conditions at a current or planned location of a person linked to or associated with the health profile. The rules engine 203 and the remote computer 201 are configured to transmit the self-care recommendations through a data network 103 to a client device 101 wherein the client device 101 may display the self-care recommendations onto a display screen or provide an audible message conveying the self-care recommendations to a user.

The following example is meant for illustrative purposes only and should not be used to limit the scope of the claimed inventions.

A user named John runs a software application "app" on his client device (e.g., his iphone).

John has also filled out a health profile associated with his unique login name and the data contained in the health profile is stored in a remote database.

The app is configured to transmit at certain time intervals (e.g., once per day or on demand as requested by John) a physical location which is determined by a GPS sensor within John's iphone through a cellular data network to a remote computer (e.g., a server). John may also enter by text or voice his current or planned location into his iphone and have that location transmitted to the remote computer.

The remote computer comprises operating code and a rules engine to perform, in-part, methods and systems of the present invention. The server receives a unique identifier from John's phone (e.g., his login name) and the location of John's iphone (e.g., city, state country or latitude and longitude). The remote computer is also configured to receive environmental information from 3rd party data sources (e.g., The Weather Channel™) and will associate current and forecasted environmental conditions of the location provided by John's iphone.

The remote computer is also configured to access a database comprising John's health profile. A rules engine will run a series of rules or operating instructions to determine if any self-care recommendations should be sent to John's iphone. In this example, John's age is 75 years old and the forecasted daily high temperature at his location is 108° F. with a relative humidity value of 85%. The rules engine will compare these environmental values (in this case the weather values of temperature and relative humidity) to acceptable values for John's health profile using current medical best practices.

The rules engine may process this information as AGE=75 and lookup in a table in a database acceptable temperate ranges for a person at that age to be outside. The table may list acceptable temperature ranges as 50-70° F. for example. The rules engine may then run the following sample operating code:

IF AGE >74 and IF TEMP >71° F.
THEN transmit SELF-CARE RECOMMENDATION
"Warning high temperatures expected for today. Stay indoors in air-conditioning".

John's iphone may then display onto a screen this warning or self-care recommendation as a text or by other visual or audible means.

In an further example, if the temperature at John's location was expected to be 60° F. for the day, the rules engine of the invention is configured to transmit positive or motivational messages to encourage healthy living and self-care. In this alternative example, the system of the invention may run this operating code:

IF AGE >10 but <85 and if TEMP >50° F. but <70° F.
THEN transmit SELF-CARE RECOMMENDATION
"It's a great day to take a walk. Take a friend for twice the fun!"

John's iphone may then display onto a screen this positive self-care ecommendation as text or by other visual or audible means.

The above examples illustrate only a few embodiments of the invention and it should be understood to one of ordinary skill in the art that the present invention includes many other forms of self-care recommendations which can be both warnings or positive and motivational in nature.

Other embodiments can be used to help acclimate a person to a new environment which may be significantly different from their home environment (i.e., where they normally reside). In this embodiment, a client device 101 is used to transmit a current or expected future location through a data network 103 to a remote computer 201. The remote computer may access a health profile in a database 202 associated with a person (generally though a unique identifier such as login name). The remote computer 201 is configured to receive data from environmental data providers 301. Using a set of rules generally stored in a database 202 or software code, a rules engine 203 will determine if the current or planned location of a person is significantly different in distance (e.g., greater than 50, 100, 150 , or 200 miles) or elevation (e.g., greater than 500, 1000, 1500, 2000 ft) from their home location associated with their health profile and if certain conditions apply (as defined by rules in a database or software code) the rules engine 203 will instruct the remote computer 201 to transmit acclimation recommendations to the client device 101. For example, if a person with a home residence in Chicago, Ill. is traveling to Phoenix, Ariz., the rules engine 203 will compare average temperatures, humidity, UV index, etc. between the two locations and transmit an acclimation recommendation such as "Make sure to drink lots of fluids. It's hot and dry out there!". A client device 101 may then display that acclimation recommendation as text or by other visual or audible means.

The intent of the acclimation recommendation feature of the present invention is to promote healthy self-care activities for a person to enjoy greater harmony with a new environment.

Alternative embodiments may be performed without the need of a remote computer. In such embodiments, a client device is configured to run software code (e.g., an app) and store one or more health profiles onto an internal storage device (e.g., a hard drive or flash drive). The client device is configured to receive GPS location information and will run an internal rules engine based on software code (which may be updated from time to time) and receive environmental data from a 3rd party provider. It is therefore within the scope of the invention for a client device to generate its' own set of self-care recommendations and acclimation recommendations to be displayed to user without relying on a remote computer for processing.

Figure 2:
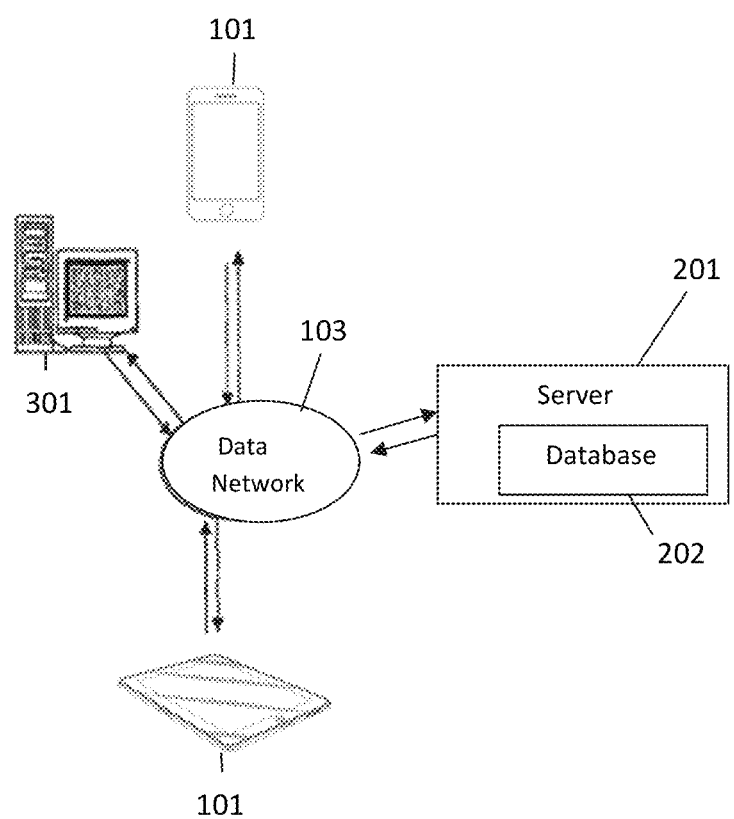
FIG. 2 illustrates an example of some of the components for the system of the present invention.

When referring to FIG. 2, in one embodiment, the system 100 comprises one or more client devices 101, a data network 103, a remote computer 201, a database 202, and a environmental data provider 301.

The methods and systems as described above are preferably implemented in software, and accordingly one of the preferred implementations of the invention is as a set of instructions (operating code) in a code module resident in the random access memory of a programmable computer such as a remote computer or a client device. Until required by the computer, the set of instructions may be stored in another computer memory, e.g., in a hard disk drive, or in a removable memory such as an optical disk (for eventual use in a CD or DVD ROM) or floppy disk (for eventual use in a floppy disk drive), a removable storage device (e.g., external hard drive, memory card, or flash drive), or downloaded via the Internet or some other computer network. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the specified method steps.

The technology described and claimed herein is not to be limited in scope by the specific preferred embodiments herein disclosed, since these embodiments are intended as illustrations, and not limitations, of several aspects of the technology. Any equivalent embodiments are intended to be within the scope of this technology. Indeed, various modifications of the technology in addition to those shown and described herein will become apparent to those skilled in the art from the foregoing description. Such modifications are also intended to fall within the scope of the appended claims.

What is claimed is:

1. A computer implemented method to provide acclimation recommendations to a person currently located in a different geographical region than their home region, the method comprising:
    sensing a current location of the person with a sensor of a client device;
    linking the current location to a unique identifier;
    transmitting the current location and unique identifier through a data network to a remote computer;
    associating said unique identifier with a health profile for the person stored on said remote computer;
    determining an environmental condition for said current location;
    comparing the environmental condition to an acceptable value based on the person's health profile;
    determining an acclimation recommendation specific for said person based on said comparison of said environmental condition to said acceptable value; and
    transmitting said acclimation recommendation to the client device to be displayed on a screen of the client device to be viewed by the person.

2. The method of claim 1, wherein the acceptable value is associated with an age, height, weight or body mass index range for the person.

3. The method of claim 1, which includes storing the person's age, height and weight in the person's health profile.

4. The method of claim 1, wherein the environmental condition includes a present environmental condition.

5. The method of claim 1, wherein the environmental condition includes a forecasted environmental condition.

6. The method of claim 1, wherein comparing the environmental condition to the acceptable value includes determining whether a present or forecasted temperature or humidity for the current location is above or below a predetermined threshold for the person.

7. The method of claim 1, wherein comparing the environmental condition to the acceptable value includes determining whether a present or forecasted temperature or humidity for the current location is within a predetermined range for the person.

8. The method of claim 1, wherein comparing the environmental condition to the acceptable value includes determining whether a present or forecasted temperature or humidity for the current location is above or below a predetermined threshold associated with the person's age.

9. The method of claim 1, which includes determining whether the person's current location is within a predetermined distance from the person's home region, and transmitting said acclimation recommendation if the person's current location is not within the predetermined distance.

10. The method of claim 1, wherein the environmental condition includes an air condition.

11. The method of claim 1, wherein the environmental condition includes a water condition.

12. The method of claim 1, wherein the environmental condition includes at least one of: (i) a water body condition; (ii) a UV index; (iii) an ozone level; (iv) an allergen count; and (v) a mold particle count.

13. The method of claim 1, wherein the environmental condition includes at least one of: (i) temperature; (ii) precipitation; (iii) wind speed; (iv) wind direction; (v) humidity; (vi) relative humidity; (vii) cloud cover; and (viii) sun exposure.

14. A computer implemented method to provide acclimation recommendations to a person currently located in a different geographical region than their home region, the method comprising:
    sensing a current location of the person with a sensor of a client device;
    linking the current location to a unique identifier;
    transmitting the current location and unique identifier through a data network to a remote computer;
    associating said unique identifier with a health profile for the person stored on said remote computer;
    determining a temperature or humidity at said current location;
    comparing the determined temperature or humidity to an acceptable temperature or humidity based on the person's health profile;
    determining an acclimation recommendation specific for said person based on said comparison of said determined temperature or humidity to said acceptable temperature or humidity; and
    transmitting said acclimation recommendation to the client device to be displayed on a screen of the client device to be viewed by the person.

15. The method of claim 14, wherein the determined temperature or humidity is a current temperature or humidity.

16. The method of claim 14, wherein the determined temperature or humidity is a forecasted temperature or humidity.

17. The method of claim 14, wherein comparing the determined temperature or humidity to the acceptable temperature or humidity includes determining whether the determined temperature or humidity is above or below the acceptable temperature or humidity.

18. The method of claim 14, wherein the acceptable temperature or humidity includes a temperature or humidity range, and wherein comparing the determined temperature or humidity to the acceptable temperature or humidity includes determining whether the determined temperature or humidity falls within the temperature or humidity range.

19. The method of claim 14, wherein comparing the environmental condition to the acceptable value for the person's age includes determining whether a temperature or humidity at the current location falls within a temperature or humidity range associated with the person's age.

20. A computer implemented method to provide acclimation recommendations to a person currently located in a different geographical region than their home region, the method comprising:

sensing a current location of the person with a sensor of a client device;

linking the current location to a unique identifier;

transmitting the current location and unique identifier through a data network to a remote computer;

associating said unique identifier with a health profile for the person stored on said remote computer;

determining an environmental condition for said current location;

determining the person's age from the person's health profile;

comparing the environmental condition to an acceptable value for the person's age;

determining an acclimation recommendation specific for said person based on said comparison of said environmental condition to said acceptable value for the person's age; and transmitting said acclimation recommendation to the client device to be displayed on a screen of the client device to be viewed by the person.

* * * * *